United States Patent [19]

Dunn et al.

[11] Patent Number: 5,565,184

[45] Date of Patent: Oct. 15, 1996

[54] FUNCTIONALIZED TRIPODAL LIGANDS FOR X-RAY & RADIOACTIVE IMAGING APPLICATIONS

[75] Inventors: T. Jeffrey Dunn, Cedar Hill; Dennis A. Moore, Ferguson; Muthunadar P. Periasamy, Chesterfield; Milorad M. Rogic, Town and Country; Rebecca A. Wallace, Manchester; David H. White; Steven R. Woulfe, both of Ballwin, all of Mo.

[73] Assignee: Mallinckrodt Medical, Inc., St. Louis, Mo.

[21] Appl. No.: 310,514

[22] Filed: Sep. 22, 1994

Related U.S. Application Data

[62] Division of Ser. No. 87,837, Jul. 2, 1993, Pat. No. 5,405,601.

[51] Int. Cl.$^6$ ............................................. A61K 49/04
[52] U.S. Cl. .................. 424/1.65; 424/9.42; 436/173; 514/492; 514/504; 514/836; 534/16
[58] Field of Search ........................ 424/1.65, 9.42; 436/173; 128/653.4, 654; 514/492, 504, 836; 534/16

[56] References Cited

U.S. PATENT DOCUMENTS

| | | | |
|---|---|---|---|
| 3,725,290 | 4/1973 | Nelson et al. | 252/110 |
| 3,974,090 | 8/1976 | Mitchell | 252/389 A |
| 5,198,208 | 3/1993 | Berg et al. | 424/1.1 |

FOREIGN PATENT DOCUMENTS

| | | |
|---|---|---|
| 0299795 | 1/1989 | European Pat. Off. . |
| 0462787 | 12/1991 | European Pat. Off. . |
| 0465295 | 1/1992 | European Pat. Off. . |
| 91/16075 | 10/1991 | WIPO . |

OTHER PUBLICATIONS

Kaplan et al., *Chem. Abstracts*, 111:127027e (1989).
Matsumura, S.; *Yukagaku*, 28(6):403–406 (1979).
Satoru, K. et al., *Chem. Abstracts*, 113:31858s (1990).
Chiu, K. W. et al. *Chem. Abstracts*, 117:146345x (1992).
Geraldes, C. F. G. C. et al., *Chem. Abstracts* 117:199431d (1992).
Smith et al., *Inorganic Chemistry*, 27(22):3929–3934 (1988).

*Primary Examiner*—Gary E. Hollinden
*Attorney, Agent, or Firm*—Brian K. Stierwalt

[57] ABSTRACT

The present invention provides new and structurally diverse compositions comprising compounds of the general formula:

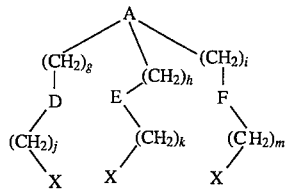

wherein A is N or $CR_1$, $R_1$ is hydrogen, $C_1$–$C_8$ alkyl, or $C_6$–$C_{10}$ aryl, where the alkyl or aryl group may be optionally substituted with one or more hydroxy, $C_1$–$C_8$ alkyl, $C_1$–$C_8$ hydroxyalkyl, $C_1$–$C_8$ alkoxy, $C_6$–$C_{10}$ aryl, $C_6$–$C_{10}$ hydroxyaryl, $C_6$–$C_{10}$ aryloxy, $-CO_2R_2$, $-CONR_3R_4$, or $NR_3R_4$; $R_2$–$R_7$ are as defined within; g, h, i, j, k and m may be the same or different and are an integer from one to about six; X is $-CO_2H$, $-PO_3H_2$, $-SO_3H$ or $-CONHOH$.

Methods for imaging including MRI, X-ray and radiation diagnosis using compositions of the invention are also provided.

13 Claims, No Drawings

FUNCTIONALIZED TRIPODAL LIGANDS FOR X-RAY & RADIOACTIVE IMAGING APPLICATIONS

This is a divisional of application Ser. No. 08/087,837 filed Jul. 2, 1993, U.S. Pat. No. 5,405,601.

FIELD OF THE INVENTION

This invention relates to magnetic resonance imaging (MRI), x-ray imaging, and radiopharmaceuticals. More particularly the invention relates to methods and compositions for enhancing MRI, x-ray imaging, and radiopharmaceuticals.

BACKGROUND OF THE INVENTION

The use of contrast agents in diagnostic medicine is rapidly growing. In X-ray diagnostics, for example, increased contrast of internal organs, such as the kidneys, the urinary tract, the digestive tract, the vascular system of the heart (angiography), and so forth is obtained by administering a contrast agent which is substantially radiopaque. In conventional proton MRI diagnostics, increased contrast of internal organs and tissues may be obtained by administering compositions containing paramagnetic metal species which increase the relaxivity of surrounding protons. In ultrasound diagnostics, improved contrast is obtained by administering compositions having acoustic impedances different than that of blood and other tissues.

The recently developed technique of MRI encompasses the detection of certain atomic nuclei utilizing magnetic fields and radio-frequency radiation. It is similar in some respects to X-ray computed tomography (CT) in providing a cross-sectional display of the body organ anatomy with excellent resolution of soft tissue detail. As currently used, the images produced constitute a map of the proton density distribution, the relaxation times, or both, in organs and tissues. The technique of MRI is advantageously non-invasive as it avoids the use of ionizing radiation.

While the phenomenon of NMR was discovered in 1945, it is only recently that it has found application as a means of mapping the internal structure of the body as a result of the original suggestion of Lauterbur (*Nature*, 242, 190–191 [1973]). The fundamental lack of any known hazard associated with the level of the magnetic and radio-frequency fields that are employed renders it possible to make repeated scans on vulnerable individuals. In addition to standard scan planes (axial, coronal, and sagittal), oblique scan planes can also be selected.

With an MRI experiment, the nuclei under study in a sample (e.g. protons) are irradiated with the appropriate radio-frequency (RF) energy in a highly uniform magnetic field. These nuclei, as they relax, subsequently emit RF at a sharp resonance frequency. The resonance frequency of the nuclei depends on the applied magnetic field.

According to known principles, nuclei with appropriate spin, when placed in an applied magnetic field (B, expressed generally in units of gauss or Tesla [$10^4$ gauss]) align in the direction of the field. In the case of protons, these nuclei precess at a frequency, f, of 42.6 MHz, at a field strength of 1 Tesla. At this frequency, an RF pulse of radiation will excite the nuclei and can be considered to tip the net magnetization out of the field direction, the extent of this rotation being determined by the pulse duration and energy. After the RF pulse, the nuclei "relax" or return to equilibrium with the magnetic field, emitting radiation at the resonant frequency. The decay of the emitted radiation is characterized by two relaxation times, i.e., $T_1$, the spin-lattice relaxation time or longitudinal relaxation time, that is, the time taken by the nuclei to return to equilibrium along the direction of the externally applied magnetic field, and $T_2$, the spin-spin relaxation time associated with the dephasing of the initially coherent precession of individual proton spins. These relaxation times have been established for various fluids, organs and tissues in different species of mammals.

In MRI, scanning planes and slice thicknesses can be selected. This selection permits high quality transverse, coronal and sagittal images to be obtained directly. The absence of any moving parts in MRI equipment promotes high reliability. It is believed that MRI has a greater potential than CT for the selective examination of tissue characteristics in view of the fact that in CT, X-ray attenuation coefficients alone determine image contrast, whereas at least five separate variables ($T_1$, $T_2$, proton density, pulse sequence and flow) may contribute to the MRI signal.

By reason of its sensitivity to subtle physicochemical differences between organs and/or tissues, it is believed that MRI may be capable of differentiating different tissue types and in detecting diseases which induce physicochemical changes that may not be detected by X-ray or CT which are only sensitive to differences in the electron density of tissue.

As noted above, two of the principal imaging parameters are the relaxation times, $T_1$ and $T_2$. For protons (or other appropriate nuclei), these relaxation times are influenced by the environment of the nuclei, (e.g., viscosity, temperature, and the like). These two relaxation phenomena are essentially mechanisms whereby the initially imparted radio-frequency energy is dissipated to the surrounding environment. The rate of this energy loss or relaxation can be influenced by certain other nuclei which are paramagnetic. Chemical compounds incorporating these paramagnetic nuclei may substantially alter the $T_1$ and $T_2$ values for nearby protons. The extent of the paramagnetic effect of a given chemical compound is a function of the environment.

In general, paramagnetic species such as ions of elements with atomic numbers of 21 to 29, 42 to 44 and 58 to 70 have been found effective as MRI image contrasting agents. Examples of suitable ions include chromium(III), manganese(II), manganese(III), iron(II), iron(III), cobalt(II), nickel(II), copper(II), praseodymium(III), neodymium(III), samarium(III), and ytterbium(III). Because of their very strong magnetic moments, gadolinium(III), terbium(III), dysprosium(III), holmium(III) and erbium(III) are preferred. Gadolinium(III) ions have been particularly preferred as MRI contrasting agents.

Typically, paramagnetic ions have been administered in the form of complexes with organic complexing agents. Such complexes provide the paramagnetic ions in a soluble, non-toxic form, and facilitate their rapid clearence from the body following the imaging procedure. Gries et al., U.S. Pat. No. 4,647,447, disclose complexes of various paramagnetic ions with conventional aminocarboxylic acid complexing agents. A preferred complex disclosed by Gries et al. is the complex of gadolinium(III) with diethylenetriamine-pentaacetic acid ("DTPA").

Paramagnetic ions, such as gadolinium(III), have been found to form strong complexes with DTPA, ethylenediaminetetraacetic acid ("EDTA"), and with tetraazacyclododecane-N,N',N",N"'-tetraacetic acid ("DOTA").

These complexes do not dissociate substantially in physiological aqueous fluids. The gadolinium complex of DTPA has a net charge of −2, whereas the gadolinium complex of EDTA or DOTA has a net charge of −1, and both are generally administered as soluble salts. Typical salts are sodium and N-methylglucamine. The administration of salts is attended by certain disadvantages. These salts can raise the in vivo ion concentration and cause localized disturbances in osmolality, which in turn, can lead to edema and other undesirable reactions.

Efforts have been made to design new ionic and neutral paramagnetic metal complexes which avoid or minimize the above mentioned disadvantages. In general, this goal can be achieved by converting one or more of the free carboxylic acid groups of the complexing agent to neutral, non-ionizable groups. For example, S. C. Quay, in U.S. Pat. Nos. 4,687,658 and 4,687,659, discloses alkylester and alkylamide derivatives, respectively, of DTPA complexes. Similarly, published Dean et al., U.S. Pat. No. 4,826,673 discloses mono- and polyhydroxyalkylamide derivatives of DTPA and their use as complexing agents for paramagnetic ions. It can also be achieved by covalent attachment of organic cations to the complexing agent in such a manner that the sum of positive and negative charges in the resulting metal complex is zero.

The nature of additional substituents in the complexing agent can have a significant impact on tissue specificity. Hydrophilic complexes tend to concentrate in the interstitial fluids, whereas lipophilic complexes tend to associate with cells. Thus, differences in hydrophilicity can lead to different applications of the compounds. See, for example, Weinmann et al., *AJR*, 142, 679 (Mar. 1984) and Brasch, et al., *AJR*, 142, 625 (Mar. 1984).

Finally, toxicity of paramagnetic metal complexes is greatly affected by the nature of the complexing agents. In vivo release of free metal ions from the complex is a major cause of toxicity. Four principal factors are important in the design of chelates for making paramagnetic metal complexes that are highly stable in vivo and less toxic. The first three factors are thermodynamic in nature whereas the fourth involves chelate kinetics. The first factor is the thermodynamic stability constant of the metal-ligand. The thermodynamic stability constant indicates the affinity that the totally unprotonated ligand has for a metal. The second factor is the conditional stability constant which takes into account the pH and is important when considering stability under physiological pH. The selectivity of the ligand for the paramagnetic metal over other endogenous metal ions such as zinc, iron, magnesium and calcium is the third factor. In addition to the three thermodynamic considerations, complexes with structural features that make in vivo transmetallation reactions much slower than their clearance rates would be predicted to have low toxicities. Therefore, in vivo reaction kinetics are a major factor in the design of stable complexes. See, for example, Cacheris et al., *Magnetic Resonance Imaging*, 8:467 (1990) and Oksendal, et al., *JMRI*, 3:157 (1993).

A need continues to exist for new and structurally diverse compounds for use as imaging agents. There is a further need to develop highly stable complexes with good relaxivity and osmolar characteristics.

SUMMARY OF THE INVENTION

The present invention provides new and structurally diverse compositions comprising compounds of the general formula:

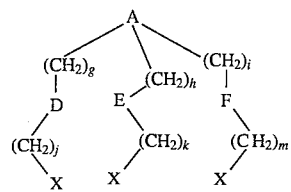

wherein A is N or $CR_1$, $R_1$ is hydrogen, $C_1$–$C_8$ alkyl, or $C_6$–$C_{10}$ aryl, where the alkyl or aryl group may be optionally substituted with one or more hydroxy, $C_1$–$C_8$ alkyl, $C_1$–$C_8$ hydroxyalkyl, $C_1$–$C_8$ alkoxy, $C_6$–$C_{10}$ aryl, $C_6$–$C_{10}$ hydroxyaryl, $C_6$–$C_{10}$ aryloxy, $—CO_2R_2$, $—CONR_3R_4$, or $NR_3R_4$; $R_2$, $R_3$, and $R_4$ may be the same or different and are hydrogen, $C_1$–$C_8$ alkyl, $C_1$–$C_8$ hydroxyalkyl and $C_1$–$C_8$ alkoxyalkyl, $R_3$ and $R_4$ may form a 5 or 6 membered carbocyclic ring optionally containing singularly or in combination nitrogen, oxygen or sulfur; D is O, $—O(CH_2)_2O—$, $—O(CH_2)_3O—$, or $NR_5$; E is O, $—O(CH_2)_2O—$, $—O(CH_2)_3O—$ or $NR_6$; F is O, $—O(CH_2)_2O—$, $—O(CH_2)_3O—$ or $NR_7$;

$R_5$, $R_6$, and $R_7$ may be the same or different and are hydrogen, $C_1$–$C_8$ alkyl, or $C_6$–$C_{10}$ aryl, where the alkyl or aryl group may be optionally substituted with one or more hydroxy, $C_1$–$C_8$ alkyl, $C_1$–$C_8$ hydroxyalkyl, $C_1$–$C_8$ alkoxy, $C_6$–$C_{10}$ aryl, $C_6$–$C_{10}$ hydroxyaryl, $C_6$–$C_{10}$ aryloxy, $—CO_2R_2$, $—CONR_3R_4$, or $—NR_3R_4$, $—SH$, $—PO_3H_2$, $—SO_3H$ or $—CONHOH$; g, h, i, j, k and m may be the same or different and are an integer from one to about six; X is $—CO_2H$, $—PO_3H_2$, $—SO_3H$ or $—CONHOH$.

Also provided are compositions comprising complexes of the compounds with metal ions of the general formula

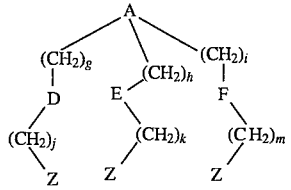

wherein A is N or $CR_1$, wherein $R_1$ is hydrogen, $C_1$–$C_8$ alkyl, or $C_6$–$C_{10}$ aryl, where the alkyl or aryl group may be optionally substituted with one or more hydroxy, $C_1$–$C_8$ alkyl, $C_1$–$C_8$ hydroxyalkyl, $C_1$–$C_8$ alkoxy, $C_6$–$C_{10}$ aryl, $C_6$–$C_{10}$ hydroxyaryl, $C_6$–$C_{10}$ aryloxy, $—CO_2R_2$, $—CONR_3R_4$, or $NR_3R_4$; $R_2$, $R_3$, and $R_4$ may be the same or different and are hydrogen, $C_1$–$C_8$ alkyl, $C_1$–$C_8$ hydroxyalkyl and $C_1$–$C_8$ alkoxyalkyl, $R_3$ and $R_4$ may form a 5 or 6 membered carbocyclic ring optionally containing singularly or in combination nitrogen, oxygen or sulfur; D is O, $—O(CH_2)_2O—$, $—O(CH_2)_3O—$ or $NR_5$; E is O, $—O(CH_2)_2O—$, $—O(CH_2)_3 O—$ or $NR_6$, F is O, $—O(CH_2)_2O—$, $—O(CH_2)_3O—$ or $NR_7$; $R_5$, $R_6$, and $R_7$ may be the same or different and are hydrogen, $C_1$–$C_8$ alkyl, or $C_6$–$C_{10}$ aryl, where the alkyl or aryl group may be optionally substituted with one or more hydroxy, $C_1$–$C_8$ alkyl, $C_1$–$C_8$ hydroxyalkyl, $C_1$–$C_8$ alkoxy, $C_6$–$C_{10}$ aryl, $C_6$–$C_{10}$ hydroxyaryl, $C_6$–$C_{10}$ aryloxy, $—CO_2R_2$, $—CONR_3R_4$, or $—NR_3R_4$, $—SH$, $—PO_3H_2$, $—SO_3H$ or $—CONHOH$; g, h, i, j, k and m may be the same or different and are selected from an integer from one to about six; Z is $—CO_2Y$, $—PO_3HY$, $—SO_3Y$ or $—CONHOY$; and Y is a metal ion equivalent and/or a physiologically acceptable cation of an inorganic or organic base.

Compositions comprising the above formulas wherein Y is a radioactive metal ion, a paramagnetic ion, or a metal ion capable of absorbing x-rays are also provided for use as radiopharmaceuticals, magnetic resonance imaging, and x-ray contrast agents, respectively.

Diagnostic compositions comprising the compounds of the invention are also provided. Methods of performing diagnostic procedures with compositions of the invention are also disclosed. The methods comprise administering to a patient an effective amount of the compositions of the invention and subjecting the patient to an imaging procedure.

DETAILED DESCRIPTION

The compositions of the invention are suitable for use with a variety of modalities including x-rays, magnetic resonance imaging and radiopharmaceuticals.

The functionality of the R groups of the compositions of the invention afford the additional capability of derivatization to biomolecules and synthetic polymers. Biomolecule refers to all natural and synthetic molecules that play a role in biological systems. Biomolecules include hormones, amino acids, peptides, peptidomimetics, proteins, deoxyribonucleic acid (DNA) ribonucleic acid (RNA), lipids, albumins, polyclonal antibodies, receptor molecules, receptor binding molecules, monoclonal antibodies and aptamers. Specific examples of biomolecules include insulins, prostaglandins, growth factors, liposomes and nucleic acid probes. Examples of synthetic polymers include polylysine, arborols, dendrimers, and cyclodextrins. The advantages of using biomolecules include enhanced tissue targeting through specificity and delivery. Coupling of the chelating moieties to biomolecules can be accomplished by several known methods (e.g., Krejcarek and Tucker *Biochem. Biophys. Res. Comm*, 30, 581 (1977); Hnatowich, et al. *Science*, 220, 613 (1983). For example, a reactive moiety present in one of the R groups is coupled with a second reactive group located on the biomolecule. Typically, a nucleophilic group is reacted with an electrophilic group to form a covalent bond between the biomolecule and the chelate. Examples of nucleophilic groups include amines, anilines, alcohols, phenols, thiols and hydrazines. Electrophilic group examples include halides, disulfides, epoxides, maleimides, acid chlorides, anhydrides, mixed anhydrides, activated esters, imidates, isocyanates and isothiocyanates. And finally, the compositions of the invention should provide the additional advantage of being kinetically inert.

Examples of suitable alkyl groups for use with the invention include methyl, ethyl, propyl, isopropyl, butyl, cyclohexyl, heptyl and octyl. Suitable alkoxy groups include methoxy, ethoxy, propoxy, butoxy, pentoxy, hexoxy, heptoxy and octoxy. Hydroxyalkyl groups suitable for use with the invention include both mono and poly hydroxyalkyls such as hydroxyethyl, 2-hydroxypropyl, 2,3-dihydroxypropyl, 2,3,4-trihydroxybutyl, tris(hydroxymethyl)methyl and 2-hydroxy-1-hydroxymethylethyl. Suitable alkoxyalkyl groups include methoxymethyl, 2,3-dimethoxypropyl, tris (methoxymethyl)methyl, and 2-methoxy-1-methoxymethylethyl.

Examples of suitable compounds of the invention are N',N'',N'''-tris (carboxymethyl) —N,N,N-tris[[[(2-hydroxyphenyl)methyl]amino]ethyl]amine, N',N'',N'''-tris(carboxymethyl)-N,N,N tris[[[hydroxyethyl] amino] ethyl] amine, 1,1,1- tris[2,5-dioxo-6-carboxyhexyl]ethane, 2,2,2-tris[2,5-dioxo-6-carboxyhexyl] ethanol, N,N,N',N'-tetrakis (carboxymethyl)- 2-carboxymethoxy-1,3-diaminopropane, 1,9-bis[(2-methoxyethyl)amino]-1,9-dioxo- 3,7-diaza-5-(carboxymethoxy)-3,7-bis(carboxymethyl)nonane, N,N,N', N'-tetrakis(carboxymethyl)- 2-(carboxymethyl)amino-1,3-diaminopropane, 1,9-bis[ (2,3-dihydroxypropyl)amino] -1,9-dioxo- 3,7-diaza-5-(carboxymethyl)amino-3,7-bis(carboxymethyl)nonane, and N,N',N''-tris(carboxymethyl)-1,1,1 -tris[(methylamino)methyl] ethane. These compounds are generally referred to as ligands.

Complexes of the novel ligands or compounds of the invention with one or more central metal ions or metal ion equivalents such as paramagnetic metals praseodymium(III), neodymium(III), samarium(III), ytterbium(III) terbium(III), dysprosium(III), holmium(III), erbium(III), iron(II), iron(III), manganese(II), manganese(III), gadolinium(III), chromium(III), cobalt(II) and nickel(II) are useful for enhancing magnetic resonance images. While such metal ions are themselves paramagnetic in nature and capable of altering the magnetic resonance signal characteristics of body tissues, organs or fluids, they may exhibit significant toxicity when administered in the form of ionic salts. However, novel complexes of the invention are relatively or substantially nontoxic and therefore useful for enhancing magnetic resonance images by favorably altering relaxation times $T_1$ and $T_2$ and affording improved contrast between normal and diseased tissues or organs.

The preferred complexes of the invention are those formed from the above ligands and iron(II), iron(III), manganese(II), manganese(III) and gadolinium(III) as the central metal ion or ions. Depending upon the particular ligand employed and the particular central metal ion used, the complexes formed may be neutral, ionic, cationic, or zwitterionic in nature, or they may be negatively charged. The neutral complexes are generally preferred and generally appear to exhibit relatively lower toxicity as compared to ionic or negatively charged complexes. The negatively charged complexes formed by the ligands and central metal ions enumerated above may be further complexed with one or more cations of an inorganic or organic base which are physiologically tolerated. Examples of cations for further complexing include sodium, potassium, calcium, and salts of N-methylglucamine, and diethanolamine.

Examples of preferred compounds of the invention and one or more central metal ions (i.e., complexes) include N,N'',N'''-tris(carboxymethyl)-N,N,N-tris[[[(2-hydroxyphenyl)methyl]amino]ethyl]amine, gadolinium complex,
N,N'',N''' tris(carboxymethyl)-N,N,N-tris[[[hydroxyethyl] amino]ethyl]amine, dysprosium complex,
1,1,1-tris [2,5-dioxo-6-carboxyhexyl] ethane, gadolinium complex,
2,2,2-tris[2,5-dioxo-6-carboxyhexyl]ethanol, dysprosium complex,
N,N,N',N'-tetrakis(carboxymethyl)-2-carboxymethoxy-1,3-diaminopropane, gadolinium complex, dimeglumine salt,
1,9-bis[(2-methoxyethyl)amino]-1,9-dioxo-3,7-diaza-5-(carboxymethoxy)- 3,7-bis(carboxymethyl)nonane, gadolinium complex,
N,N,N',N'-tetrakis(carboxymethyl)-2-(carboxymethyl)amino- 1,3-diaminopropane, dysprosium complex, disodium salt,
1,9-bis[2,3-dihydroxypropyl)amino] -1,9-dioxo-3,7-diaza-5-carboxymethyl)amino- 3,7-bis (carboxymethyl)nonane, iron complex, and
N,N',N'' -tris(carboxymethyl)-1,1,1-tris[(methylamino)methyl] ethane, dysprosium complex.

In addition to their utility in magnetic resonance imaging procedures, the compositions of the invention can also be employed for delivery of either radiopharmaceuticals or heavy metals for x-ray contrast into the body. For use in diagnostic and therapeutic radiopharmaceuticals the complexed metal ion must be radioactive. Radioisotopes of the elements technetium, rhenium, indium, gallium, copper, yttrium, samarium and holmium are suitable. For use as X-ray contrast applications the complexed metal ion must be able to absorb adequate amounts of the X-rays. These metal ions are generally refered to as radioopaque. Suitable elements for use as the radioopaque metal ion include lead, bismuth, gadolinium, dysprosium, holmium and praseodymium.

Examples of preferred compounds for radiopharmaceuticals are

N',N'',N'''-tris(carboxymethyl)-N,N,N-tris[[[(2-hydroxyphenyl)methyl]amino] ethyl] amine, technetium complex, N',N'',N'''-tris (carboxymethyl)-N,N,N-tris[[ [hydroxyethyl] amino] ethyl] amine, indium complex, 1, 1, 1-tris[2,5-dioxo-6-carboxyhexyl]ethane, gallium complex, N,N,N',N'-tetrakis(carboxymethyl)-2-carboxymethoxy- 1,3-diaminopropane, rhenium complex, and N,N',N''-tris(carboxymethyl)-1, 1, 1-tris[(methylamino)methyl] ethane, yttrium complex.

Examples of preferred compounds for x-ray contrast agents are

N',N'',N'''-tris (carboxymethyl)-N,N,N-tris[ [ [ (2-hydroxyphenyl)methyl]amine] ethyl] amine, lead complex, N',N'',N'''-tris(carboxymethl)-N,N,N-tris[[[hydroxyethyl] amino]ethyl]amine, gadolinium complex, 1,9-bis[(2,3-dihydroxypropyl)amino]-1,9-dioxo-3,7-diaza-5-carboxymethyl)amino-3,7-bis(carboxymethyl)nonane, dysprosium complex, and 1,9-bis[ (2-methoxyethyl)amino] -1,9-dioxo-3,7-diaza-5-(carboxymethoxy)- 3,7-bis (carboxymethyl)nonane, bismuth complex.

The compositions of the invention can be formulated into diagnostic compositions for enteral or parenteral administration. These compositions contain an effective amount of the paramagnetic ion complex along with conventional pharmaceutical carriers and excipients appropriate for the type of administration contemplated. For example, parenteral formulations advantageously contain a sterile aqueous solution or suspension of from about 0.05 to about 1.0M of a paramagnetic ion complex according to this invention. Parenteral compositions may be injected directly or mixed with a large volume parenteral composition for systemic administration. Preferred parenteral formulations have a concentration of paramagnetic ion complex of about 0.1M to about 0.5M. Such solutions also may contain pharmaceutically acceptable buffers and, optionally, electrolytes such as sodium chloride. The compositions may advantageously contain a slight excess (e.g., from about 0.01 to about 15.0 mole % excess) of a complexing agent or its complex with a physiologically acceptable, non-toxic cation. Such physiologically acceptable, non-toxic cations include calcium ions, magnesium ions, copper ions, zinc ions, salts of n-methylglucamine and diethanolamine, and the like. Generally, calcium ions are preferred.

Formulations for enteral administration may vary widely, as is well-known in the art. In general, such formulations are liquids which include an effective amount of the paramagnetic ion complex in aqueous solution or suspension. Such enteral compositions may optionally include buffers, surfactants, thixotropic agents, and the like. Compositions for oral administration may also contain flavoring agents and other ingredients for enhancing their organoleptic qualities.

The diagnostic compositions are administered in doses effective to achieve the desired enhancement of the NMR image. Such doses may vary widely, depending upon the particular paramagnetic ion complex employed, the organs or tissues which are the subject of the imaging procedure, the NMR imaging procedure, the NMR imaging equipment being used, and the like. In general, parenteral dosages will range from about 0.001 to about 1.0 mMol of paramagnetic ion complex per kg of patient body weight. Preferred parenteral dosages range from about 0.01 to about 0.5 mMol of paramagnetic ion complex per kg of patient body weight. Enteral dosages generally range from about 0.5 to about 100 mMol, preferably from about 1.0 to about 10 mMol, preferably from about 1.0 to about 20.0 mMol of paramagnetic ion complex per kg of patient body weight.

The diagnostic compositions of the invention are used in the conventional manner. The compositions may be administered to a patient, typically a warm-blooded animal, either systemically or locally to the organ or tissue to be imaged, and the patient then subjected to the NMR imaging procedure. Protocols for imaging and instrument procedures are found in texts such as Stark, D. D.; Bradley, W. G. *Magnetic Resonance Imaging;* Mosby Year Book: St. Louis, Mo., 1992.

Radiopharmaceutical Imaging Procedures are found in Fred A. Mettler, Jr., M.D., M.P.H., Milton J. Guiberteau, M.D., *Essentials of Nuclear Medicine Imaging,* Grune and Stratton, Inc., New York, N.Y. 1983) and E. Edmund Kim, M.S., M.D. and Thomas P. Haynie, M.D., (MacMillan Publishing Co. Inc., New York, N.Y. 1987).

XRCM Imaging Procedures are found in Albert A. Moss, M.D., Gordon Gamsu, M.D., and Harry K. Genant, M.D., *Computed Tomography of the Body,* (W. B. Saunders Company, Philadelphia, Pa. 1992) and M. Sovak, Editor, *Radiocontrast Agents,* (Springer-Verlag, Berlin 1984).

The following examples illustrate the specific embodiments of the invention described in this document. As would be apparant to skilled artisans, various changes and modifications are possible and are contemplated within the scope of the invention described.

EXAMPLES

Example 1

Synthesis of 1,5-diaza-3-(carboxymethyl)oxa-1,5-(tetracarboxymethyl)pentane

A mixture of 1,3-diamino-2-hydroxypropane (1.00g, 0.011 mol), phthalic anhydride(3.26 g, 0.022 mol) and triethylamine (0.11 g, 0.15 ml, 0.001 mol) in 30 mL toluene was heated in an oil bath at 120° C. using a Dean-Stark trap to remove water as it formed. After 7 hrs, the mixture was cooled to room temperature and the solids were filtered. Recrystallization from methylene chloride/hexane gave 1,3-diphthalimido-2-hydroxypropane.

To a solution of 1,3-diphthalimido-2-hydroxypropane (0.50 g, 1.40 mmol) in 10 mL of anhydrous tetrahydrofuran under nitrogen atmosphere is added 97% sodium hydride (0.04 g, 1.54 mmol). After 30 minutes, t-butylbromoacetate (0.27 g, 0.22 mL, 1.40 mmol) is added and the mixture is refluxed for 8 hrs. The reaction mixture is partitioned between methylene chloride and water and the organic layer is separated. The organic layer is washed with water, dried over anhydrous sodium sulfate and evaporated under reduced pressure to give 1,3-diphthalilmido-2-(t-butylcarboxymethyl)oxapropane.

A mixture of 1,3-diphthalimido-2-(t-butylcarboxymethyl)oxapropane( 0.50 g, 1.08 mmol) and 55% hydrazine (0.23 mL, 4.6 mmol) in 2 mL of methanol is refluxed for 4 hrs. After cooling the reaction solution to room temperature, the solids are filtered and the filtrate is evaporated under reduced pressure to yield 1,3-diamino-2-(t-butylcarboxymethyl)oxapropane.

A solution of 1,3-diamino-2-(t-butylcarboxymethyl)oxapropane (0.20 g, 0.98 mmol) in 5 mL of water is adjusted to pH 10 with 1N sodium hydroxide. Bromoacetic acid (0.16 g, 3.90 mmol) is added and the mixture is stirred at 25° C. for 12 hrs., keeping the pH>9 with 1N sodium hydroxide. The pH of the solution is adjusted to 7 with 1N hydrochloric acid and then the solution is passed through a short bed of Amberlite IR- 120 (H+ form) resin. The water is removed under reduced pressure to give 1.5-diaza-3-(carboxymethyl)oxa-1,5-(tetracarboxymethyl)pentane.

Example 2

Synthesis of 1,5-diaza-3-(carboxymethyl)oxa-1,5-(tetracarboxymethyl)pentane, gadolinium(III) disodium salt A slurry of 1,5-diaza-3-(carboxymethyl)oxa-1,5-(tetracarboxymethyl) pentane (0.40 g, 0.92 mmol), sodium hydroxide (0.74 g, 1.84 mmol) and gadolinium(III) oxide (0.17 g, 0.46 mmol) in 5 mL of deionized water is heated at 80° C. under nitrogen atmosphere for 15 hrs. The clear solution is evaporated under reduced pressure to yield a glass. This material is dissolved in deionized water and purified through reversed phase packing to give 1,5-diaza- 3-(carboxymethyl)oxa-1,5-(tetracarboxymethyl)pentane, gadolinium(III) disodium salt.

Example 3

Synthesis of 1,9-bis[(2-methoxyethyl)amino]-1,9-dioxo-3,7-diaza-5-(carboxymethyl)oxa-3,7-(dicarboxymethyl) nonane To a slurry of 1,5-diaza-3-(carboxymethyl)oxa-1,5-(tetracarboxymthyl)pentane (0.40 g, 1.05 mmol) in 5mL of pyridine is added acetic anhydride (0.32 g, 0.30 mL, 3.15 mmol). The mixture is heated at 55° C. for 5 hrs. The resulting solids are filtered, washed with acetonitrile and dried in a vacuum desiccator at 1 mm to give 1,3-bis-( 2,6-dioxomorpholino)-2-(carboxymethyl)oxapentane.

A mixture of 1,3-bis-(2,6-dioxomorpholino)-2-(carboxymethyl)oxapentane (0.45 g, 1.30 mmol) and 2-methoxyethylamine (0.19 g, 0.22 mL, 2.60 mmol) in 5 mL of 2-propanol is heated at 80° C. for 12 hrs. After cooling the reaction mixture to room temperature, the solid is filtered, washed with 2-propanol and dried in a vacuum desiccator at 1 mm to give 1,9-bis[(2-methoxyethyl)amino] -1,9-dioxo-3,7-diaza-5-(carboxymethyl)oxa- 3,7-(dicarboxymethyl) nonane.

Example 4

Synthesis of 1,9-bis[2-methoxyethyl)amino]-1,9-dioxo- 3,7-diaza-5-(carboxymethyl)oxa-3,7-(dicarboxymthyl)nonane, bismuth(III) salt A slurry of 1,9-bis[ (2-methoxyethyl)amino] -1,9-dioxo-3,7-diaza-5-(carboxymethyl)oxa-3,7-dicarboxymethyl) nonane (0.50 g, 1.01 mmol) and bismuth(III) oxide (0.12 g, 0.50 mmol) in 10 mL of deionized water was heated at 80° C. under nitrogen atmosphere for 15 hrs. The solution is evaporated under reduced pressure to yield a glass. The glass is dissolved in deionized water and purified through reversed phase packing to give 1,9-bis[(methoxyethyl)amino]-1,9-dioxo-3,7-diaza-5-(carboxymethyl)oxa- 3,7-(dicarboxymethyl)nonane, bismuth(III) salt.

Example 5

Synthesis of 1,5-diaza-3-(carboxymethyl)amino-1,5-(tetracarboxymethyl)pentane

To a solution of 1,3-diphthalimido-2-hydroxypropane (1.00 g., 2,86 mmol) in 80 mL of acetone was added Jones reagent (chromium trioxide and sulfuric acid) until an orange color persisted. The excess oxidant was removed by the addition of 2-isopropanol until a green color was obtained and the solvents were evaporated under reduced pressure. The residue was partitioned between methylene chloride and water and the layers were separated. The organic layer was washed with water, dried over anhydrous sodium sulfate and evaporated under reduced pressure to give 1,3-diphthalimido-3-oxopropane.

A solution of 1,3-diphthalimido-2-oxopropane (0.70 g, 2.00 mmol) and glycine t-butyl ester (0.26 g, 2.00 mmol) in 20 mL of methanol is stirred at 25° C. for 15 hrs. Then solid sodium borohydride (0.15 g, 4.00 mMol) is added and the solution is aain stirred at 25° C. for 15 hrs. The solvent is removed under reduced pressure to give 1,3-diphthalimido-3-(t-butoxycarboxymethyl)aminopropane.

A mixture of 1,3-diphthalimido-2-(butoxycarboxymethyl)aminopropane (0.65 g, 1.40 mmol) and 55% hydrazine (0.36 mL, 6.30 mmol) in 5 mL of methanol is refluxed for 5 hrs. After cooling the slurry to room temperature, the solids are filtered and the filtrate is evaporated under reduced pressure to yield 1,3-diamino-2-(t-butoxycarboxymethyl)aminopropane.

A solution of 1,3-diamino-2-(t-butoxycarboxymethyl)aminopropane (0.30 g, 1.48 mmol) in 5 mL of water is adjusted to pH 10 with 1N sodium hydroxide. Bromoacetic acid (0.82 g, 5.92 mmol) is added and the mixture is stirred at 25° C. for 15 hrs., keeping the pH>9 with 1N sodium hydroxide. The pH of the mixture is brought to 7 with in 1N hydrochloride acid and then the solution is passed through a short bed of Amberlite IR-120 (H+form) resin. The water is evaporated under reduced pressure to give 1,5-diaza-3-(carboxymethyl)amino- 1,5-(tetracarboxymethyl)pentane.

Example 6

Synthesis of 1,5-diaza-3-(carboxymethyl)amino-1,5-(tetracarboxymehyl)pentane, ytterbium(III) disodium salt A slurry of 1,5-diaza-3-(carboxymethyl)amino-1,5-(tetracarboxymethyl)pentane (0.50 g, 1,32 mmol), sodium hydroxide (0.11 g, 2.64 mmol) and ytterbium oxide (0.26 g, 0.66 mmol) in 5 mL of deionized water is heated at 80° C. under nitrogen atmosphere for 15 hrs. The solution is evaporated under reduced pressure. The resulting glass is dissolved in deionized water and purified through reversed phase packing to give 1,5-diaza-3-(carboxymethyl)amino-1,5-(tetra-carboxymethyl)pentane, ytterbium(III) complex, disodium salt.

Example 7

Synthesis of 1,9-bis[(2,3-dihydroxypropyl)amino]-1,9-dioxo- 3,7-diaza-5-(carboxymethyl)-amino-3,7-(dicarboxymethyl)nonane To a slurry of 1,5-diaza-3-(carboxymethyl)amino-1,5-(tetracarboxymethyl)pentane (0.50 g, 1.32 mmol) in 5 mL of pyridine is added acetic anhydride (0.40 g, 0.37 mL, 3.96 mmol). The mixture is heated at 55° C. for 5 hrs. The resulting solids are filtered, washed with acetonitrile and dried in a vacuum desiccator in 1 mm to give 1,3-bis-(2,6-dioxomorpholino)-2-(carboxymethyl)aminopentane.

A mixture of 1,3-bis(2,6-dioxomorpholino)-2(carboxymethyl)aminopentane (0.45 g, 1.30 mmol) and 1-amino- 2,3-dihydroxypropane(0.24 g, 2.6 mmol) in 5 mL of 2-propanol is heated at 80° C. for 12 hrs. The resulting solid is filtered after cooling the reaction flask to room temperature. The solid is washed with 2-propanol and dried in a vacuum desiccator at 1 mm to yield 1,9-bis[(2,3-dihydroxypropyl)amino]-1,9-dioxo-3,7-diaza-5-(carboxymethyl)amino-3,7-(dicarboxymethyl)nonane.

Example 8

Synthesis of 1,9-bis[(2,3-dihydroxypropyl)amino] -1,9-dioxo- 3,7-diaza-5-(carboxymethyl)-amino-3,7-dicarboxymethyl)nonane, gadolinium(III) complex A slurry of 1,9-bis[ (2,3-dihydroxypropyl)amino] - 1,9-dioxo-3,7-diaza-5-(carboxymethyl)amino-3,7-(dicarboxymethyl)nonane (0.50 g, 0.95 mmol) and gadolinium oxide (0.17 g, 0.48 mmol) in 5 mL of deionized water is heated at 80° C. under nitrogen atmosphere for 15 hrs. The clear solution is then evaporated under reduced pressure. The resulting glass is purified through reversed phase packing using water as eluant to yield 1,9-bis-[(2,3-dihydroxypropyl)amino]-1,9-dioxo-3,7-diaza- 5-(carboxymethyl)amino-3,7-(dicarboxymethyl)nonane, gadolinium(III) complex.

Example 9

Synthesis of 1,1,1-{tris- [2,5-dioxo)-6-carboxyhexyl]} ethane.

To a slurry of 5.00 g NaH (60% dispersion in oil) in 250 mL dry, distilled dimethylformanide (DMF), is added 17.0 mL (18.2 g, $1.20 \times 10^{-1}$ mole) 2-benzyloxyethanol. After stirring for 1 hr. the mixture is filtered to remove unreacted NaH. The filtrate is added to a stirred solution consisting of 5.00 mL (6.53 g, $3{,}62 \times 10^2$ mole) 1,1,1-tris(chloromethyl)ethane in 100 mL DMF. After the addition is complete the mixture is allowed to stir overnight. The solvent is removed by evaporation at reduced pressure. The residue is dissolved in ethyl acetate, 200 mL, and the solution washed with water. The organic layer is collected, dried with sodium sulfate, filtered and concentrated to 50 mL. The solution is diluted with 50 mL hexanes and the mixture chromatographed on silica using a flash method. Fractions are tested for product content by thin layer chromatography (tlc) and appropriately combined. The combined fractions are filtered and evaporated to leave 1,1,1-{tris[1-(2,5-dioxo)- 4-phenylhexyl]}ethane.

A solution 1,1,1-{tris[1-(2,5-dioxo)-4-phenylhexyl]ethane, 10.4 g ($1.99 \times 10^{-2}$ mole) in 50 mL 95% ethanol is shaken with 5 g 10% Pd on C at 55 psi hydrogen gas overnight. After removing the catalyst by filtration and solvent by evaporation the remaining 1,1,1-{tris[1-( 2-oxo)-4-hydroxybutyl]}ethane is collected.

1,1,1-{tris[1-(2-oxo)-4-hydroxybutyl]}ethane, 5.00 g ($1.98 \times 10^{-2}$ mole) is treated with potassium hydroxide, 4.00 g ($6.06 \times 10^{-2}$ mole, 85%) in 50 mL dimethyl sulfoxide (DMSO). To this mixture is added benzyl bromoacetate, 9.90 mL (14.31 g, $6.24 \times 10^{-2}$ mole). The progress of the reaction is followed by thin layer chromatography (tlc). When the reaction is complete, the mixture is evaporated at reduced pressure, to a sludge and poured over ice (500 g). The resulting precipitate is collected by filtration and washed with water until the filtrate is neutral in pH. The crude solid is collected, dissolved in ethyl acetate (150 mL) and dried overnight with magnesium sulfate. After filtering, to remove the drying agent, hexanes is added to effect crystalliztion of 1,1,1-{tris[1-(2,5-dioxo)-6-(carboxybenzyl)-hexyl]}ethane.

1,1,1- {tris- [1-(2,5-dioxo)-6-(carboxybenzyl)hexyl]}ethane, 8.00 g ($1.15 \times 10^{-2}$ mole) is shaken with 5.00 g 10% Pd on C in ethanol-water (70:30), 25 mL, at 55 psi hydrogen gas, overnight. The mixture is filtered to remove catalyst and the filtrate evaporated to give a tacky residue. The residue is crystallized from a minimum of boiling acetonitrile to afford 1,1,1-{tris-[2,5-dioxo)-6-carboxyhexyl]}ethane.

Example 10

Synthesis of aqua(gadolinium(III)[1,1,1-(tris-[1-(2,5-dioxo)- 6-carboxylatohexyl] } -ethane] }

The complex is made by allowing the reaction of 2.60 g ($7.00 \times 10^{-3}$ mole) gadolinium trichloride hexahydrate with 3.00 g ($7.00 \times 10^{-3}$ mole) of 1,1,1-{tris[1-(2,5-dioxo)- 6-carboxyhexyl]}ethane, in a mixture of 0.84 g ($2.10 \times 10^{-2}$ mole) sodium hydroxide in 25 mL methanol. The resulting precipitate is removed by filtration and the filtrate reduced in volume to effect crystallization.

Example 11

Synthesis of aqua{gadolinium(III) [2,2,2-{tris [1-(2,5-dioxo)-carboxylato-hexyl]}ethanol]

A mixture of 2-[(benzyloxy)methyl]-2-(hydroxymethyl-1,3-propanediol (Dunn, T. J., Neumann, W. L., Rogic, M. M., Woulfe, S. R. *J. Org. Chem.* 1990, 55, 6368), 10.0 g ($4.42 \times 10^{-2}$ mole) and 18.3 g ($1.32 \times 10^{-1}$ mole) potassium carbonate are slurried in 200 mL DMSO in a 1L round bottom flask. The mixture is heated to 40° C. and a solution containing 15.4 mL (23.3 g, 0.140 mole) bromoethyl acetate in 100 mL DMSO is added dropwise. The mixture is allowed to stir overnight. Solvent is removed from the reaction mixture by evaporation at reduced pressure. The residue is dissolved in 100 mL ethyl acetate and washed with water to remove residual DMSO. The organic layer is dried with magnesium sulfate. After filtering to remove the drying agent, the solution is concentrated and treated with hexanes to effect crystallization of 2,2,2-(tris[1-(2-oxo- 4-acetoxybutyl)]}ethylbenzyl ether.

A slurry consisting of 5.00 g ($3.10 \times 10^{-2}$ mole) of 2,2,2-{tris[1-(2-oxo-4-acetoxybutyl)]}ethylbenzyl ether, in 100 mL 0.5N sodium hydroxide is allowed to stir until hydrolysis is complete by tlc. To the solution is added enough 1.0N hydrochloric acid to make pH=2. The solution is saturated with sodium chloride and extracted with 4×100 mL dichloromethane. The combined organic extracts are dried with magnesium sulfate overnight. After filtering the mixture to remove drying agent, the solvent is removed by evaporation under reduced pressure. The residue is dissolved in 100 mL DMSO and 14.2 (0.102 g mole) potassium carbonate is added. The mixture is stirred and warmed to 40° C. To the mixture is added a solution of 15.8 mL (19.0 g, 0.0977 mole) t-butyl bromoacetate in 50 mL DMSO. The progress of the reaction is followed by tlc. When the reaction is complete, the solvent is removed by evaporation under reduced pressure. The residue is suspended in 200 mL ethyl acetate and washed with 4×100 mL distilled water. The organic layer is collected and treated with sodium sulfate overnight. The mixture is filtered to remove the drying agent, concentrated by evaporation and treated with hexanes to effect crystallization of 2,2,2-{tris[1-(2,5-dioxo)-(carboxy-tbutyl) hexyl]}ethylbenzyl ether.

A solution containing 15.0 g ($2.18 \times 10^{-2}$ mole) of 2,2,2-{tris [1-2,5-dioxo)-(6-carboxy-t-butyl)hexyl]}ethylbenzyl ether, in 100 mL methanol, is shaken with 5.00 g 10% Pd on C at 55 psi hydrogen overnight. The solution is filtered to remove the catalyst and the mixture evaporated to afford 2,2,2-{tris [1-(2,5-dioxo)-(6-carboxy-t-butyl)hexyl] }ethanol.

A mixture consisting of 15 mL trifluoroacetic acid and 13.3 g of 2,2,2-{tris[1-(2,5-dioxo)-(6-carboxy-t-butyl)hexyl]}ethanol, is allowed to stir for four hours. The mixture is evaporated to dryness and the residue dissolved in 100 mL methanol. To the solution is added 8.1 g $2.18 \times 10^{-2}$ mole) gadolinium trichloride hexahydrate, and the mixture allowed to stir for two hours. At this time 2.62 g ($6.55 \times 10^{-2}$ mole) sodium hydroxide is added. The resulting precipitate of sodium chloride is removed by filtration and the filtrate concentrated to effect crystallization of aqua{gadolinium(III)[2,2,2-{tris[1-( 2,5-dioxo)-6-carboxy-lato-hexyl]}ethanol].

Example 12

Synthesis of N',N'',N'''-tris (carboxymethyl)-N,N,N-tris [[[(2-hydroxyphenyl)methyl] amino] ethyl amine hydrochloride salt.

Tris (aminoethyl)amine (14.6 g, 100 mmol) and salicylaldehyde (39.0 g, 320 mmol) were refluxed in 500 mL of methanol for ten minutes. Slow cooling afforded bright yellow crystals. The solid was isolated by filtration and dried to give 40.3 g. (88%) of N,N,N-tris[[ [ (2-hydroxyphenyl) methylene] amino] ethyl] amine.

A solution of N,N,N-tris[[[(2hydroxyphenyl)methylene] amino]ethyl]amine (40.0 g, 87 mmol) in 250 mL of methanol and 250 mL of methylene chloride was cooled in an ice bath. Sodium borohydride (10.0 g, 263 mmol) was added in several portions. Stirring was continued at room temperature for two hours. The solvents were evaporated and the residue was taken up in ether. This solution was washed with water and brine, dried over magnesium sulfate, filtered and evaporated to afford N,N,N-tris[[[(2-hydroxyphenyl)methyl] amino]ethyl]amine(30.0 g, 74%) as a colorless glass.

A mixture of N,N,N-tris[ [ [ (2-hydroxyphenyl) methyl amino] ethyl] amine (6.0 g, 13 mmol), t-butyl bromoacetate (8.1 g, 42 mmol) and diisopropylethylamine (5.4 g, 42 mmol) in 90 mL of acetonitrile was refluxed for four hours. The solvent was evaporated and the residue was taken up into ether. The solution was washed with water and brine, dried over magnesium sulfate, filtered and evaporated to afford a thick oil that solidified on standing. The solid was recrystallized from ethyl acetate/hexanes to give 8.4 g (81%) of N',N'',N'''-tris(t-butoxycarbonylmethyl)-N,N,N-tris [[[(2-hydroxyphenyl)methyl] amino] ethyl] amine: mp 84°–88° C.

A solution of N',N'',N'''-tris(t-butoxycarbonylmethyl)-N,N,N-tris[[[(2-hydroxyphenyl) methyl] amino] ethyl] amine (8.0 g, 10 mmol) and anisole (5 mL) in 50 mL of trifluoroacetic acid is stirred for five hours at room temperature. The solvents are evaporated and the residue is dissolved in 50 mL of dilute hydrochloric acid. This solution is washed with ethyl acetate and evaporated to afford N',N'',N'''-tris(carboxymethyl)-N,N,N-tris[[[(2-hyrdroxyphenyl)methyl] amino] ethyl ] amine hydrochloride salt.

Example 13

Synthesis of N',N'',N'''-tris(carboxymethyl)-N,N,N-tris [[[(2-hydroxyphenyl) methyl] amino] ethyl] amine, gadolinium complex N,N'',N''''-tris(carboxymethyl)-N,N,N-tris[[[(2-hydroxyphenyl)methyl]amino]ethyl]amine hydrochloride salt (7.8 g, 10 mmol) is dissolved in 100 mL of water. The pH is adjusted to 4 by the addition of 5% sodium bicarbonate solution. Gadolinium oxide (3.6 g, 10 mmol) is added and the milky suspension is heated at 70° C. for 24 hours. The solution is filtered and evaporated. The residue is purified by $C_{18}$ chromatography to afford N,N'',N''''-tris(carboxymethyl)-N,N,N-tris[[[(2hydroxyphenyl)methyl]amino]ethyl] amine, gadolinium complex.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A method for delivering radiopharmaceuticals to a patient which comprises administering to a patient a compound of the general formula

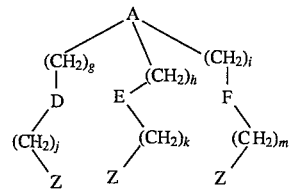

wherein A is $CR_1$, $R_1$ is hydrogen, $C_1$–$C_8$ alkyl, or $C_6$–$C_{10}$ aryl, where the alkyl or aryl group may be optionally substituted with one or more hydroxy, $C_1$–$C_8$ alkyl, $C_1$–$C_8$ hydroxyalkyl, $C_1$–$C_8$ alkoxy, $C_6$–$C_{10}$ aryl, $C_6$–$C_{10}$ hydroxyaryl, $C_6$–$C_{10}$ aryloxy, —$CO_2R_2$, —$CONR_3R_4$, or $NR_3R_4$;

$R_2$, $R_3$, and $R_4$, may be the same or different and are hydrogen, $C_1$–$C_8$ alkyl, $C_1$–$C_8$ hydroxyalkyl and $C_1$–$C_8$ alkoxyalkyl; D is O, —$O(CH_2)_2O$—, or —$O(CH_2)_3O$—; E is O, —$O(CH_2)_2O$—, or —$O(CH_2)_3O$—; F is O, —$O(CH_2)_2O$— or —$O(CH_2)_3O$—; g, h, i, j, k, and m may be the same or different and are selected from an integer from one to about six; Z is —$CO_2Y$, —$PO_3HY$, —$SO_3Y$ or —CONHOY; and Y is a metal ion equivalent and/or a physiologically acceptable cation of an inorganic or organic base, with the proviso that at least one Y is a metal ion equivalent of a nonalkali metal.

2. The method of claim 1 wherein A is $CR_1$, $R_1$ is $CH_3$, D is —$O(CH_2)_2O$—, E is —$O(CH_2)_2O$—, F is —$O(CH_2)_2O$—, g is 1, h is 1, i is 1, j is 1, k is 1, m is 1, Z is $CO_2Y$, and Y is gallium.

3. The method of claim 1 wherein the metal is indium.

4. The method of claim 1 wherein the metal is technetium.

5. The method of claim 1 wherein the metal is rhenium.

6. The method of claim 1 wherein A is $CR_1$, $R_1$ is $CH_3$, D is —$O(CH_2)_2O$—, E is —$O(CH_2)_2O$—, F is —$O(CH_2)_2O$—, g is 1, h is 1, i is 1, j is 1, k is 1, m is 1, Z is $PO_3HY$ and Y is technetium.

7. The compound of claim 1 wherein A is $CR_1$, $R_1$ is $CH_3$, D is —$O(CH_2)_2O$—, E is —$O(CH_2)_2O$—, F is —$O(CH_2)_2O$—, g is 1, h is 1, i is 1, j is 1, k is 1, m is 1, Z is —$SO_3Y$, and Y is rhenium.

8. The compound of claim 1 wherein A is $CR_1$, $R_1$ is $CH_2OH$, D is —$O(CH_2)_2O$—, E is —$O(CH_2)_2O$—, F is —$O(CH_2)_2O$—, g is 1, h is 1, i is 1, j is 1, k is 1, m is 1, Z is—CONHOY, and Y is gallium.

9. The method of claim 1 wherein A is $CR_1$, $R_1$ is $CH_3$, D is $-O(CH_2)_2O-$, E is $-O(CH_2)_2O-$, F is $-O(CH_2)_2O-$, g is 1, h is 1, i is 1, j is 1, k is 1, m is 1, Z is $CO_2Y$, and Y is indium.

10. A method for x-ray imaging which comprises administering to a patient compound of the general formula

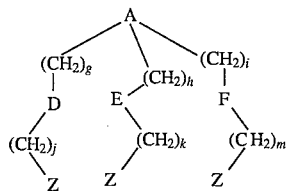

wherein A is CR, $R_1$ is hydrogen, $C_1$–$C_8$ alkyl, or $C_6$–$C_{10}$ aryl, where the alkyl or aryl group may be optionally substituted with one or more hydroxy, $C_1$–$C_8$ alkyl, $C_1$–$C_8$ hydroxyalkyl, $C_1$–$C_8$ alkoxy, $C_6$–$C_{10}$ aryl, $C_6$–$C_{10}$ hydroxyaryl, $C_6$–$C_{10}$ aryloxy, $-CO_2R_2$, $-CONR_3R_4$, or $NR_3R_4$; $R_2$, $R_3$, and $R_4$ may be the same or different and are hydrogen, $C_1$–$C_8$ alkyl, $C_1$–$C_8$ hydroxyalkyl and $C_1$–$C_8$ alkoxyalkyl, $R_3$ and $R_4$ may form a 5 or 6 membered carbocyclic ring optionally containing singularly or in combination nitrogen, oxygen or sulfur; D is O, $-O(CH_2)_2O-$, $-O(CH_2)_3O-$ or $NR_5$; E is O, $-O(CH_2)_2O-$, $-O(CH_2)_3O-$ or $NR_6$, F is O, $-O(CH_2)_2O-$, $-O(CH_2)_3O-$ or $NR_7$; $R_5$, $R_6$, and $R_7$ may be the same or different and are hydrogen, $C_1$–$C_8$ alkyl, or $C_6$–$C_{10}$ aryl, where the alkyl or aryl group may be optionally substituted with one or more hydroxy, $C_1$–$C_8$ alkyl, $C_6$–$C_{10}$ hydroxyalkyl, $C_1$–$C_8$ alkoxy, $C_6$–$C_{10}$ aryl, $C_6$–$C_{10}$ hydroxyaryl, $C_6$–$C_{10}$ aryloxy, $-CO_2R_2$, $-CONR_3R_4$, or $-NR_3R_4$, $-SH$, $-PO_3H_2$, $-SO_3H$ or $-CONHOH$; g, h, i, j, k and m may be the same or different and are selected from an integer from one to about six; Z is $-CO_2Y$, $-PO_3HY$, $-SO_3Y$ or $-CONHOY$; and Y is a metal ion equivalent and/or a physiologically acceptable cation of an inorganic or organic base.

11. A method of claim 10 wherein A is N, D is $NR_5$, E is $NR_6$, F is $NR_7$, $R_5$ is $-CH_2CH_2OH$, $R_6$ is $-CH_2CH_2OH$, $R_7$ is $-CH_2CH_2OH$ g is 2, h is 2, i is 2, j is 1, k is 1, m is 1, Z is $CO_2Y$, and Y is gadolinium.

12. The compound of claim 10 wherein A is $CR_1$, $R_1$ is H, D is $NR_5$, E is $NR_6$, F is O, $R_5$ is $-CH_2CONR_3R_4$, $R_6$ is $-CH_2CONR_3R_4$, $R_6$ is $CH_2CONR_3R_4$, $R_3$ is H, $R_4$ is $-CH_2CH_2OCH_3$, g is 1, h is 1, j is 1, k is 1, m is 1, i is zero, Z is $CO_2Y$, and Y is dysprosium.

13. A method of claim 10 wherein A is $CR_1$, $R_1$ is $CH_3$, D is $NR_5$, E is $NR_6$, F is $NR_7$, $R_5$ is $CH_3$, $R_6$ is $CH_3$, $R_7$ is $CH_3$, g is 1, h is 1, i is 1, j is 1, k is 1, m is 1, Z is $CO_2Y$, and Y is bismuth.

\* \* \* \* \*